United States Patent [19]

Ciannella

[11] Patent Number: 4,698,056

[45] Date of Patent: Oct. 6, 1987

[54] ENTERIC FEEDING DEVICE

[75] Inventor: Michael A. Ciannella, Marlboro, Mass.

[73] Assignee: Medi-Tech, Inc., Watertown, Mass.

[21] Appl. No.: 842,557

[22] Filed: Mar. 21, 1986

[51] Int. Cl.[4] .......... A61M 5/00

[52] U.S. Cl. .......... 604/164; 604/264

[58] Field of Search .......... 604/160, 164, 280, 264, 604/270, 96, 158, 169, 170

[56] References Cited

U.S. PATENT DOCUMENTS

| | | | |
|---|---|---|---|
| 396,754 | 1/1889 | Mayfield . | |
| 2,091,373 | 10/1934 | Bried | 128/239 |
| 2,603,217 | 7/1952 | McShirley | 128/239 |
| 3,640,281 | 2/1972 | Robertson | 604/264 X |
| 3,736,939 | 6/1973 | Taylor | 128/349 |
| 3,811,450 | 5/1974 | Lord | 604/96 |
| 4,361,152 | 11/1982 | Patel | 604/99 |
| 4,540,404 | 9/1985 | Wolker | 604/164 X |

*Primary Examiner*—Stephen C. Pellegrino

[57] ABSTRACT

A gastro-enterostomy device consists of an introducing catheter, stiffening member, and separable conical tip for providing an introduction lumen of relatively large bore.

7 Claims, 5 Drawing Figures

ENTERIC FEEDING DEVICE

The invention relates to catheter devices for feeding patients by delivery of liquid nourishment, e.g., into the stomach or via a dispensing end positioned in the midsection of the small intestine. The distal end of the feeding device may be introduced percutaneously via an introducing cannula, into the patient's body via corresponding puncture openings in the stomach and abdominal walls, and manipulated into place with the aid of a guidewire.

SUMMARY OF THE INVENTION

A gastro-enterostomy device comprises an elongated stiffening member, an introducing catheter defining a central lumen sized and adapted for receiving the stiffening member therewithin, with the catheter closely surrounding the stiffening member, and a separable, generally conical introduction tip member adapted for assembly with the introducing catheter and the stiffening member at the distal end thereof for introduction into a human body via a puncture opening and adapted for separation from the introducing catheter and stiffening member within the human body, whereby for facilitating introduction of the device into the body, the device is provided with a conical tip of relatively small diameter at the distal end, and the tip member is separable within the body to provide an introduction lumen of relatively large bore.

In preferred embodiments, the tip member is sized and adapted for joining with the distal end of the introducing catheter in a press-fit joint; the tip member is sized and adapted for joining with the distal end of the stiffening member in a press-fit joint; the outer surface of the distal portion of the device, including the tip member and the adjacent portion of the catheter is substantially smooth; the outer diameters of adjacent surfaces of the introducing catheter and the introducing tip member are substantially equal; the stiffening member comprises a cannula defining a center lumen and the tip member defines a center lumen aligned the lumen of the cannula, the device thereby adapted for introduction into the body through the puncture opening along a guidewire; and the device further comprises a feeding tube sized for introduction into the body through the center lumen of the catheter after separation of the introducing tip member.

The device of the invention enables a feeding catheter to be introduced into the body of a patient relatively quickly and simply, and then manipulated into place with the aid of a fluoroscope, i.e., no endoscope is required, with less trauma to the patient, and provides a lumen having a relatively large inside diameter for placement of large stomach or jejunostomy tubes.

These and other features and advantages of the invention will be understood from the following description of a preferred embodiment, and from the claims.

PREFERRED EMBODIMENT

I FIRST BRIEFLY DESCRIBE THE DRAWINGS.

Drawings

Figure 2:
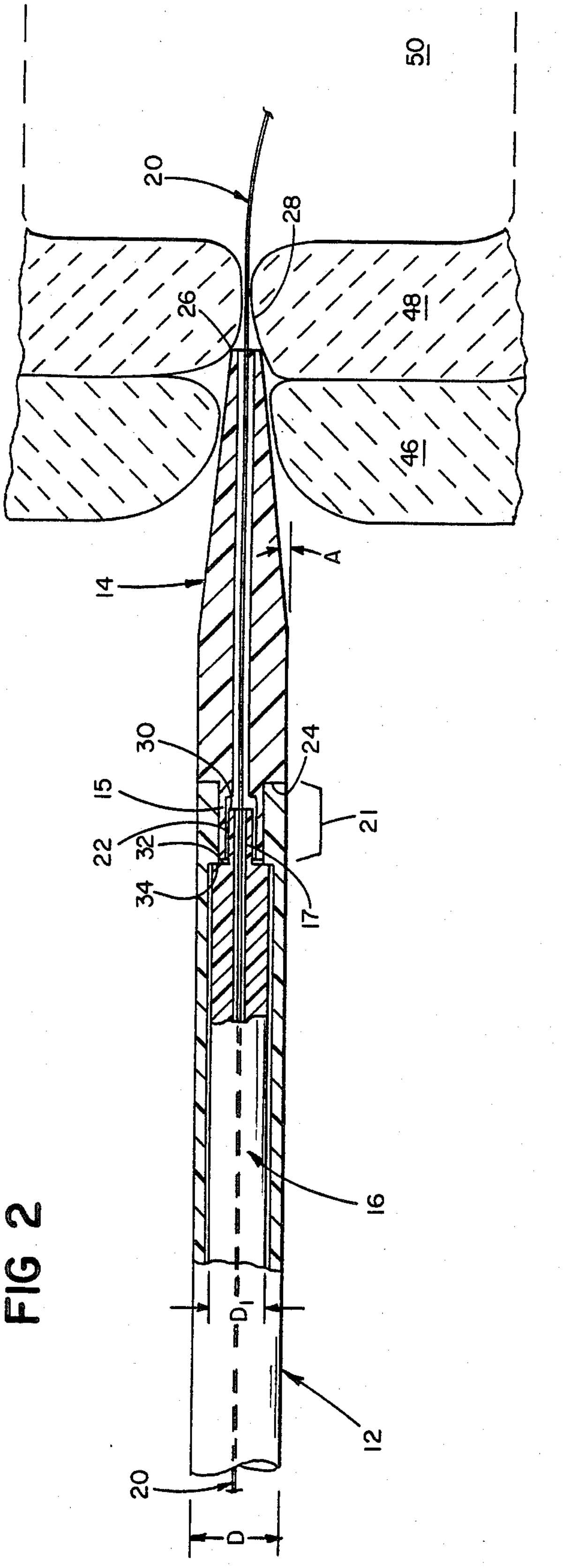
FIG. 2 is an enlarged side section view of the tip of a preferred embodiment of the cannula assembly of FIG.
Figure 3:
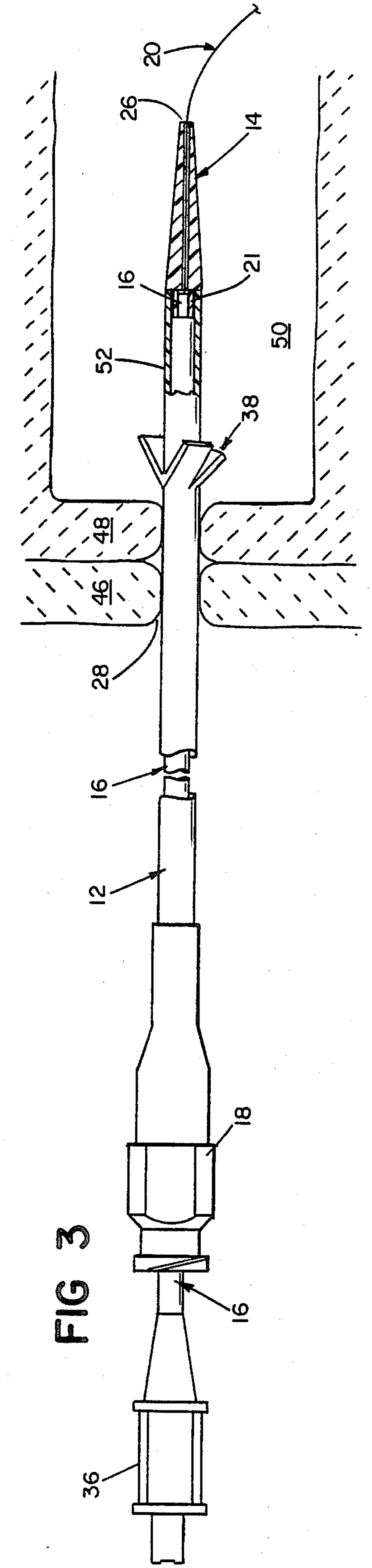
Figure 4:
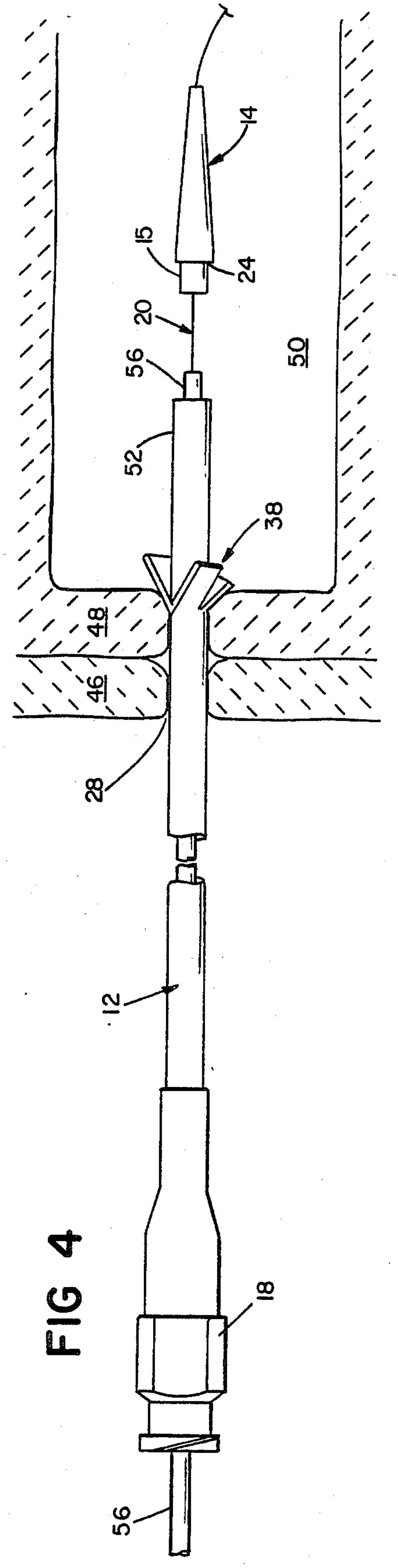
Figure 5:
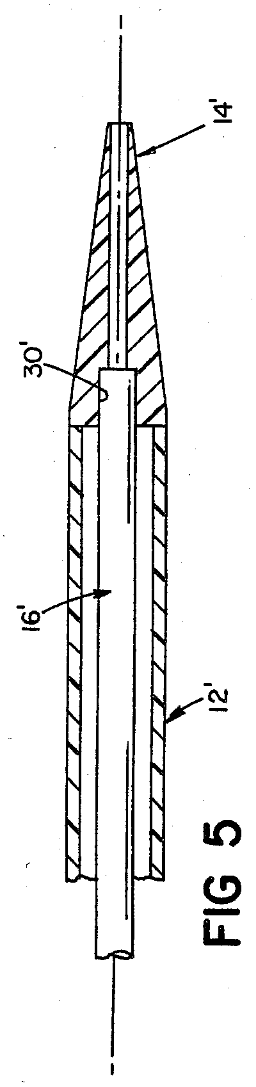

1 during insertion via corresponding puncture openings through the abdominal and stomach walls;

FIGS. 3 and 4 are similar views showing, in sequence with FIG. 2, placement of the device of the invention for enteral feeding; and FIG. 5 is an alternate embodiment of the invention.

Structure

Figure 1:
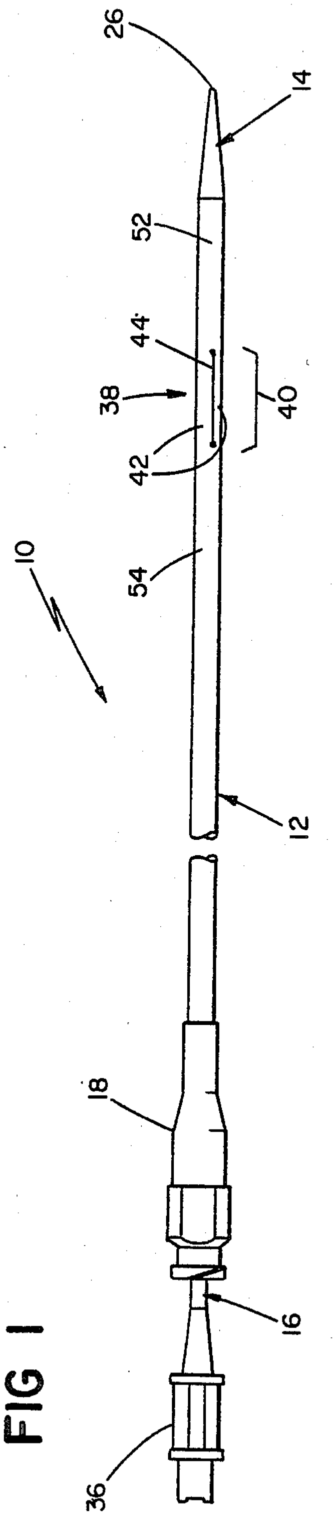
FIG. 1 is a side view of the introducing cannula assembly of the invention.

Referring to FIG. 1, assembled introducing cannula 10 consists of catheter 12, a hollow, semi-flexible tubing, detachable introduction tip member 14, and elongated straightener/stiffening member 16. Catheter 12 is equipped with a female LUER-LOK ® fitting 18 at its proximal end. The tubing forming catheter 12 is composed of polyolefin copolymer, e.g , a 50/50 mixture of polyethylene and PERCUFLEX ® (sold by Medi-Tech, Incorporated, of Watertown, Mass.) and has an outer diameter, D, in the range of between about 12 to 16 French, and may be coated on inside and outside surfaces, e.g., with silicone-based material, to promote slippage in an aqueous environment.

Referring to FIG. 2, the distal end portion of the catheter 12 includes an annular bushing segment 21 formed by thickening the wall of the catheter tubing. The inner diameter of the bushing segment forms a strengthening plinth for the distal end segment 22 of the stiffener 16, as described below, and is sized for a press fit with the proximal end portion 15 of the introduction tip, which we now describe.

Separable introduction tip member 14 is formed from narrow-bore tubing stock having an outer diameter equal to that of catheter tubing 12, and an inner bore of diameter equal to that of stiffener 16, e.g., of diameter of about 0.040 inch, sized for through passage of a guidewire 20 having diameter of about 0.038 inch. A shoulder 24 is milled from the proximal end of the tip member to provide a press fit with the distal bushing 21 of catheter 12. The distal end of tip 14 is formed to a taper of angle, A, e.g., about 5° , with a narrow distal tip end 26 to facilitate insertion through a narrow puncture opening 28 into the body. The proximal end of the tip, in the region of the shoulder, is counter bored to form an aperture 30 sized and shaped to receive the narrow distal tip portion 17 of stiffener 16, with opposed surfaces of the stiffener and the tip in close proximity, but without interfering contact.

Stiffener 16 is formed from narrow-bore tubing stock, preferably of the same composition as catheter tubing 12, and has an outer diameter, $D_1$, selected for compatibility with the inner diameter of catheter 12, i.e., stiffener 16 fits snuggly into catheter 12, without significant lateral play. The inner bore of stifffener 16 has a diameter equal to the diameter of the inner bore of the separable tip, sized for through passage of guidewire 20. The distal end of the stiffener is relieved to form a shoulder 33 which engages upon the proximal face 24 of bushing 21 when the stiffener is fully inserted. When the device is assembled, the narrowed distal end segment 17 of the stiffener 16 is disposed within the bore 30 of the tip 14, the combined mass of the components imparting relative stiffness to the assembly 10; however, the distal end segment of the stiffener is of length and diameter predetermined to avoid contact with opposed surfaces of the tip of a nature that could cause premature dislodgement of the tip from pressfit with the bushing at the distal end of the catheter. Stiffener 16 is equipped with a knurled handle 20 designed to mate with catheter end 18 such that its axial placement in tubing 12 can be quickly and reversably secured.

Referring to FIGS. 1 and 3, catheter tubing 12 further includes lock means 38 formed in the wall of tubing 12 by slitting the tubing longitudinally at region 40 over a predetermined length, e.g., 10.5 mm, at selected equidistant points, e.g., three at 120°, about the tubing circumference, as shown in FIG. 1. When the tubing segments 52, 54, respectively proximal and distal of locking means 38, are moved together, each wall portion 42 lying between slits 44 is preformed to bow radially outwardly and fold to form a region of increased diameter about the catheter tubing within the body, to thereby restrict the device from being inadvertently drawn through the opening 28.

Use

The patient is prepared for placement of the feeding tube, e.g., the liver is inspected with ultrasound or CAT-scan diagnosis to ensure that the left lobe is not unsuitably positioned; a nasal tube is positioned in the stomach through which the stomach is inflated with air; the entrance point into the stomach is selected fluoroscopically.

A corresponding incision in abdominal wall 46 is made; and the stomach wall 48 is punctured with an 18 gauge needle. A 0.038 inch diameter guidewire 20 is advanced through the bore of the needle into the stomach and the needle is removed. A hunting catheter, advanced over the guidewire into the stomach, manipulates the guidewire through the pylorus and the duodenum into the jejunum, or mid-section of the small intestine. The hunting catheter is then removed, leaving the guidewire 20 in place. member 14 is press fit into the distal bushing 21 at the end of catheter 12.

The stiffener 16 is then inserted into catheter 12, where the distal tip portion 17 of the stiffener 16 enters the bore 30 of the introduction tip member 14, and the shoulder 32 of the stiffener engages shoulder 32 of the catheter bushing. As the stiffener is further inserted into catheter 12, the distal portion 52 of the catheter is urged distally of the proximal end 54 to unfold wings 42 and draw them toward the catheter body. When stiffener 16 is fully inserted into catheter 12, it is locked in place with the wings of lock 28 straightened.

The fully assembled introducing catheter 10 is advanced over guidewire 20 into the stomach 50 until the tip 14 and lock region 40 are situated within the stomach. The stiffener 16 is removed, allowing the wings to return to their preformed, bowed-out configuration, forming lock 38 against the stomach wall. A narrow, e.g. about 8 French and 75 cm long, feeding tube 56 is advanced through the central lumen of the catheter. The advancing end of the feeding tube disengages the introduction tip member 14 from bushing 21 of catheter 12, and the tip member 14 is then passed by normal bodily function. The feeding tube 56 is advanced along the guidewire 20 until the dispensing end is situated beyond the pyloric valve, well within the jejunum. (The position can be confirmed by fluoroscopy.) Once the feeding tube is in place, the guidewire is removed, and the feeding tube secured to the abdominal wall. The nasal tube is left in place for drainage for 24 hours, following which time it is removed and feedings are begun.

Other embodiments are within the following claims, for example, in an alternate embodiment depicted in FIG. 5, the bore 30' in the proximal end of separable introducer tip member 14' is sized for press fit with the distal end of stiffener 16' and the tip is dislodged within the stomach by the action of withdrawing the stiffener from the catheter 12'.

What is claimed, is:

1. A gastro-enterostomy device comprising
an elongated stiffening member,
an introducing catheter defining an elongated central lumen sized for receiving said stiffening member therewithin, with said catheter closely surrounding said stiffening member, and
a separable, generally conical introduction tip member in a releasable assembly with the distal end of said introducing catheter and said stiffening member therewithin for introduction into a human body via a puncture opening and said introduction tip member adapted to be released from said assembly with said introducing catheter and stiffening member within said human body,
whereby, for facilitating introduction of the device into the body, said device is provided by said introduction tip member with a conical tip of relatively small diameter at the distal end, and, upon release of said tip member from assembly with said introducing catheter and stiffening member within the body, the device is provided with an introduction lumen through said introducing catheter having an inner bore diameter relatively greater than the diameter of the distal end of said conical tip member.

2. The gastro-enterostomy device of claim 1 wherein said introduction tip member and said introducing catheter are cooperatively constructed for assembly of said introduction tip member with the distal end of said introducing catheter in a press-fit joint.

3. The gastro-enterostomy of claim 1 wherein said introduction tip member and said stiffening member are cooperatively constructed for assembly of said introduction tip member with the distal end of said stiffening member in a press-fit joint.

4. The gastro-enterostomy device of claim 1 wherein the outer surface of the distal portion of said device, including said tip member and the adjacent portion of said catheter, is substantially smooth.

5. The gastro-enterostomy device of claim 1 wherein the outer diameters of adjacent surfaces of said introducing catheter and said introducing tip member are substantially equal.

6. The gastro-enterostomy device of claim 1 wherein said stiffening member comprises a cannula defining a center lumen and said tip member defines a center lumen aligned the lumen of said cannula, said device thereby adapted for introduction into the body through said puncture opening along a guidewire.

7. The gastro-enterostomy device of claim 1 further comprising a feeding tube sized for introduction into said body through the center lumen of said catheter after release of said introducing tip member.

* * * * *

UNITED STATES PATENT AND TRADEMARK OFFICE

CERTIFICATE OF CORRECTION

PATENT NO. : 4,698,056

DATED : October 6, 1987

INVENTOR(S) : Michael A. Ciannella

It is certified that error appears in the above-identified patent and that said Letters Patent are hereby corrected as shown below:

Col. 3, lines 31-32, delete "member 14 is press fit into the distal bushing 21 at the end of catheter 12." and insert instead as a new paragraph:

--The narrow proximal tip end 26 of introduction tip member 14 is press fit into the distal bushing 21 at the end of catheter 12.--

Signed and Sealed this

Twenty-ninth Day of March, 1988

*Attest:*

DONALD J. QUIGG

*Attesting Officer* *Commissioner of Patents and Trademarks*